United States Patent [19]

Fenyes et al.

[11] Patent Number: 4,505,831
[45] Date of Patent: Mar. 19, 1985

[54] METHOD OF PRESERVATION OF AQUEOUS SYSTEMS BY ADDITION TO SAID SYSTEMS OF QUATERNARY AMMONIUM SALTS OF HEXAMETHYLENETETRAMINE

[75] Inventors: Joseph G. Fenyes, Germantown; John D. Pera, Cordova, both of Tenn.

[73] Assignee: Buckman Laboratories, Inc., Memphis, Tenn.

[21] Appl. No.: 505,582

[22] Filed: Jun. 20, 1983

[51] Int. Cl.$^3$ ............................................. C10M 1/32
[52] U.S. Cl. .................................. 252/34; 252/49.3; 252/49.5; 514/244
[58] Field of Search ....................... 252/34, 49.3, 49.5; 424/249

[56] References Cited

U.S. PATENT DOCUMENTS

| | | | |
|---|---|---|---|
| 2,264,999 | 12/1941 | Musselman | 252/34 |
| 3,228,829 | 1/1966 | Wolf et al. | 252/49.5 X |
| 3,244,710 | 4/1966 | Larsen | 424/249 X |
| 3,624,253 | 11/1971 | Pawloski | 424/249 X |
| 3,624,254 | 11/1971 | Pawloski | 424/249 X |
| 3,928,607 | 12/1975 | Luloff et al. | 424/249 |
| 3,936,451 | 2/1976 | Orem et al. | 424/249 X |
| 4,062,784 | 12/1977 | Baur | 252/49.5 |
| 4,160,089 | 7/1979 | Bussi et al. | 252/49.3 X |
| 4,188,386 | 2/1980 | Engl et al. | 424/249 |

*Primary Examiner*—Andrew Metz
*Attorney, Agent, or Firm*—Finnegan, Henderson, Farabow, Garrett & Dunner

[57] ABSTRACT

Quaternary ammonium salts formed by the reaction of hexamethylenetetramine with carboxylic acids and esters, amides and nitriles substituted in the alpha position by chlorine or bromine are preservatives for aqueous solutions, emulsions, and suspensions which are susceptible to microbiological degradation.

11 Claims, No Drawings

METHOD OF PRESERVATION OF AQUEOUS SYSTEMS BY ADDITION TO SAID SYSTEMS OF QUATERNARY AMMONIUM SALTS OF HEXAMETHYLENETETRAMINE

This invention is related to new and improved methods for the preservation of aqueous solutions, emulsions, and dispersions which are susceptible to microbiological degradation.

A large number of commercial and industrial products containing such organic materials as latexes, surfactants, dispersants, stabilizers, thickeners, adhesives, starches, waxes, proteins, emulsifying agents, detergents, cellulose products, and resins are formulated in solutions, emulsions, or dispersions containing relatively large amounts of water. The temperature at which the products are stored and the pH make these products susceptible to the growth of microorganisms. These microorganisms are introduced during the manufacturing process from the air, tanks, pipes, equipment, and exposure to humans.

Microbial degradation of water containing organic products may manifest itself in a variety of problems. These include loss of viscosity, gas formation, objectionable odors, decreased pH, emulsion breaking, color change, and gelling.

Examples of aqueous solutions, emulsions, and dispersions which are subject to microbial degradation include water-based paints, latex emulsions, such as acrylic and polyvinyl acetate emulsions, adhesive solutions and emulsions, wax emulsions, polishes, cutting oil solutions and emulsions, and caulking and sealant products. Also affected are papermaking chemical products such as alum solutions, clay and pigment dispersions, starch slurries and solutions, and protein coating formations. Many of these materials are also used in other industrial and commercial products. Other solutions, emulsions and dispersions are used in petroleum production and the manufacture of detergents, surfactants, inks, and textiles.

The methods of this invention which may be used to inhibit the growth and proliferation of microorganisms in aqueous solutions, emulsions and suspensions which are susceptible to such microbiological degradation comprise adding as preservatives compounds formed by the reaction of hexamethylenetetramine and a halogen-containing compound selected from the group characterized by the formula

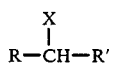

wherin X is chlorine or bromine, R is hydrogen or methyl and R' is —COOM, —CONH$_2$, —C≡N or —COOR", R" is an alkyl group containing 1 to 3 carbon atoms, and M is hydrogen, sodium, potassium or ammonium.

The hexamethylenetetramine reaction products of this invention are quaternary ammonium salts whch can be represented by the formula

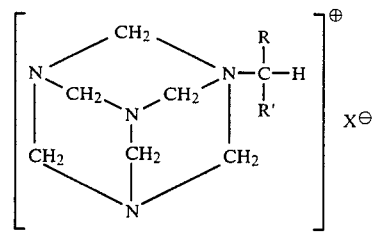

wherein R, R' and X are as described in the previous paragraph. The halogen-containing compounds which are reacted with the hexamethylenetetramine are chloroacetic acid, bromoacetic acid, 2-chloropropionic acid, 2-bromopropionic acid and the corresponding sodium, potassium and ammonium salts of the acids as well as the methyl, ethyl, 1-propyl or 2-propyl esters of the acids chloroacetamide, 2-chloropropionamide, bromoacetamide, 2-bromopropionamide, chloroacetonitrile, 2-chloropropionitrile, bromoacetonitrile, and 2-bromopropionitrile.

The salts used as preservatives in this invention are prepared by reacting approximately equimolar quantities of hexamethylenetetramine with the above-named halogen-containing compound in such inert organic solvents as methylene chloride, chloroform, methanol, and ethanol. In those instances wherein the halogen-containing compound is water soluble, the salts can be prepared in water. The temperature of these reactions can be varied from ambient to about 60° C., and the time required can vary from a few minutes to about 24 hours.

The concentration of the quaternary ammonium salts of this invention which are required to provide the preservative effect described herein will range from about 25 parts to about 5000 parts of the quaternary ammonium salt for one million parts of the solution, emulsion or suspension to be preserved. The quaternary ammonium salts are white, crystalline solids with varying degrees of hygroscopicity. The salts may be utilized as solids or may be dissolved in water prior to addition to the product being preserved. In those instances wherein the presence of water might cause some degradation of the quaternary ammonium salt over a long period of time, non-aqueous dispersions could be prepared by the proper selection of solvents, dispersants, and stabilizers which are well-known in the art as being suitable for the formation of such dispersions.

In those instances wherein the solid quaternary ammonium salts are subject to rapid degradation by heat, alkaline stabilizers such as sodium bicarbonate and sodium carbonate may be added. In addition, if aqueous solutions are subject to darkening on prolonged storage and exposure to heat, amines can be added to the solutions to prevent such discoloration.

In order to disclose the nature of the invention still more clearly, the following illustrative examples will be given. It is understood, however, that the invention is not to be limited to the specific conditions or details set forth in these examples, except insofar as such limitation are specified in the appended claims.

EXAMPLE 1

A suspension of 140.2 g. (1.0 mole) of hexamethylenetetramine and 94.5 g. (1.0 mole) of chloroacetic acid in 390 ml. of chloroform was stirred and heated at reflux temperature for 5.5 hours. The suspension was cooled and the reaction product, a white solid material, was recovered by filtration, washed with cold methylene chloride, and dried in a vacuum desiccator over wax shavings. A yield of 234.6 g. (100 percent) of the quaternary ammonium salt was obtained (m.p. 182°–184° C.).

EXAMPLE 2

A 5-liter reaction flask equipped with a water bath, thermometer, agitator, condenser, and dropping funnel was charged with 1883 g. of a 43.3 percent aqueous solution of sodium chloroacetate (7.0 moles). An aqueous solution containing 2604 g. of 37.7 percent hexamethylenetetramine was added slowly to the agitated reaction flask while maintaining the temperature at 32° to 38° C. The reaction was agitated an additional two hours at 35° C. and then cooled to 25° C. The ionic chloride was found to be 5.54 percent (Theory: 5.54 percent) indicating that the quaternization reaction was complete. The concentration of the sodium salt of the quaternary ammonium compound was 40 percent.

EXAMPLE 3

A suspension of 140.2 g. (1.0 mole) of hexamethylenetetramine and 139.0 g. (1.0 mole) of bromoacetic acid in 400 ml. of chloroform was stirred and heated at reflux temperature for 4.0 hours. The suspension was cooled and the reaction product, a white solid material, was recovered by filtration, washed with cold methylene chloride and dried in a vacuum desiccator over wax shavings. A yield of 379 g. (100 percent) of the quaternary ammonium bromide was obtained (m.p. 165°–172° C.).

EXAMPLE 4

The procedure of Example 3 was used to react 140.2 g. (1.0 mole) of hexamethylenetetramine and 93.5 g. (1.0 mole) of chloroacetamide. The quaternary ammonium chloride was obtained as a white solid (233.7 g.; 100 percent yield) with a melting point of 158°–165° C. with decomposition.

EXAMPLE 5

A suspension of 140.2 g. (1.0 mole) of hexamethylenetetramine and 75.5 g. (1.0 mole) of chloroacetonitrile in 2750 ml. of methylene chloride was stirred and heated at reflux for 4.0 hours. The suspension was cooled and the reaction product, a white solid material, was recovered by filtration, washed with cold methylene chloride and dried in a vacuum desiccator over wax shavings. A yield of 90.0 g. (42 percent) of the quaternary ammonium chloride was obtained (m.p. 158°–162° C. with decomposition.

EXAMPLE 6

The procedure of Example 3 was used to react 140.2 g. (1.0 mole) of hexamethylenetetramine and 122.6 g. (1.0 mole) of ethyl chloroacetate in 1000 ml. of chloroform. The quaternary ammonium chloride was obtained as a while solid (262.0 g.; 99.6 percent yield) with a melting point of 178°–182° C. with decomposition.

EXAMPLE 7

The preservative effectiveness of the quaternary ammonium salts of this invention was determined in a freshly prepared water-based paint formulated with titanium dioxide and calcium carbonate was pigments, an acrylic emulsion resin, dispersants and hydroxyethyl cellulose as thickener. The pH of this paint is approximately 9.0. The procedure used was as follows:

A. Weigh 100 g. of paint into prenumbered French square bottles.
B. Add the appropriate amount of the preservative to obtain the desired parts per million.
C. Add 1 ml. of inoculum. Mix well by shaking the contents of each bottle immediately after the addition of the preservative and again after the addition of the inoculum. The inoculum was prepared by adding 2 ml. of sterile saline solution to an 18- to 24-hr. agar culture of *Enterobacter aerogenes*, agitating to loosen the surface growth, and decanting to a sterile test tube. The procedure was repeated with cultures of *Pseudomanas aeruginosa* and *Bacillus subtilis*, and all three suspensions were decanted to the same test tube. The concentration of the mixed bacterial suspension was then adjusted so that a final concentration of $1 \times 10^5$ cells per ml. is achieved when one ml. of the inoculum is added to 100 ml. of the paint.
D. Include a minimum of two controls (bottles containing substrate and inoculum only).
E. Incubate at 37° C. for 9 weeks.
F. Streak from the contents of each bottle onto nutrient agar plates at intervals of 1 day, 2 days, 3 days, 7 days, and 21 days after each challenge. Incubate the streaked plates at 37° C. for 24 hours.
G. Reinoculate the test with the same test organisms at the end of 21 days and again at the end of 42 days.
H. Observe the streaked plates for growth after 24 hours of incubation.
I. Observe the contents of each bottle for
  1. Color change
  2. Odor
  3. Thickening of paint
J. Evaluate the results. A chemical is considered an effective preservative when it prevents the growth of bacteria 21 days after each inoculation.

The quaternary ammonium chlorides described in Examples 1 and 2 were effective preservatives at concentrations of 100 parts of the salt per one million parts of paint. The quaternary ammonium bromides of Example 3, 4, and 5 were effective preservatives at concentrations of 300, 50, and 50, respectively, in the paint. No color changes were noted in any of the tests. In addition, no undesirable odors were observed and the viscosities of the preserved paint samples did not change.

EXAMPLE 8

The effectiveness of the quaternary ammonium chloride of Example 1 and the sodium salt solution of Example 2 as preservatives for a large variety of organic materials in aqueous substrates were determined using a "Multiple Challenge Test". The procedure used was as follows:

A. Fifty-gram samples of the test substrate were prepared, one for each level of each preservative to be tested. An unpreserved control substrate was included in each test.
B. Prior to the first inoculation (challenge), each substrate sample was streaked onto nutrient agar with a sterile cotton swab. The agar plates were incubated at 30°–32° C. for 48 hours and observed for growth. Grossly contaminated samples were not tested further.
C. Each 50-g. substrate sample was inoculated with 0.1 ml. ($10^7$ organisms/ml.) of the mixed 24-hour culture of bacteria. The bacteria were grown previously in individual pure cultures and physically mixed immediately prior to use. Bacteria used for this test were:

| | |
|---|---|
| *Escherichia coli* | ATCC 11229 |
| *Klebsiella pneumoniae* | ATCC 23357 |
| *Pseudomonas aeruginosa* | ATCC 15442 |
| *Proteus vulgaris* | ATCC 9920 |
| *Salmonella choleraesuis* | ATCC 10708 |
| *Staphylococcus aureus* | ATCC 6538 |

D. All samples were incubated at 30°–32° C.

E. Samples were restreaked on nutrient agar 24 hours after inoculation. Samples and streaked plates were then incubated at 30°–32° C. Plates were read 48 hours after streaking and were assigned a numerical rating of 1–10 depending on the amount of microbial growth observed. A key to this rating follows:

| Rating | Number of Colonies |
|---|---|
| 1 | 0 |
| 2 | 1–4 |
| 3 | 5–10 |
| 4 | 11–25 |
| 5 | 26–50 |
| 6 | 51–100 |
| 7 | 101–200 |
| 8 | 201–300 |
| 9 | Too many to count |
| 10 | Solid mass |

F. After another 24 hours incubation samples were reinoculated with 24-hour cultures (mixed immediately prior to use). This gave 48 hours total incubation time between inoculations. The samples were streaked again 24 hours later. This procedure was repeated for 10 inoculation-incubation cycles.

G. A preservative was considered to give adequate in-use protection only if no contamination occured in the test sample during the specified inoculation-incubation cycles.

The quaternary ammonium salt of Example 1 gave adequate in-use protection (readings of "1") at the conclusion of the tests in the following substrates at a concentration of one hundred parts of salt per one million parts of substrate. The substrates were prepared by dissolving one percent of the following in water:

1. A blend of natural gums
2. A vinyl acetate-acrylate copolymer
3. Hydroxypropylmethyl cellulose
4. Hydroxyethyl ether of cornstarch
5. A high molecular weight heteropolysaccharide
6. Xanthan gum In the first experiment with the sodium salt solution of Example 2, a paper coating prepared from clay, calcium carbonate and titanium dioxide in a mixture of an acrylic resin and casein and also containing hydroxyethyl cellulose and polyphosphate was preserved after 10 challenges at a concentration of 0.025 percent of the sodium salt solution.

A solution containing 5 percent of a soluble starch was preserved with 0.1 percent of the sodium salt solution.

A cutting fluid containing 10.0 percent of organic rust inhibitor and 5.0 percent triethanolamine was diluted at the rate of one part cutting fluid with 39 parts of water. This diluted solution was preserved with 0.1 percent of the sodium salt solution. A second cutting fluid containing 20 percent of organic rust inhibitor, 10 percent of a lubricity additive and 5 percent of triethanolamine was diluted in a similar manner and the dilution was preserved with 0.05 percent of the sodium salt solution.

The invention having thus been described, what is claimed and desired to be secured by Letters Patent is:

1. A method of inhibiting the growth and proliferation of microorganisms in an aqueous system selected from the group consisting of solutions, emulsions, and suspensions which are susceptible to microbiological degradation which comprises adding to said system in an amount sufficient to inhibit the growth and proliferation of said microorganisms a quaternary ammonium compound formed by reacting in approximately equimolar quantities hexamethylenetetramine and a halogen-containing compound having the formula

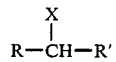

wherein X is chlorine or bromine, R is hydrogen or methyl, and R' is —COOH, —COOM, or —CONH$_2$, and wherein M is sodium, potassium, or ammonium.

2. The method of claim 1 wherein the quaternary ammonium compound is formed by the reaction of hexamethylenetetramine and chloroacetic acid.

3. The method of claim 1 wherein the quaternary ammonium compound is formed by the reaction of hexamethylenetetramine and sodium chloroacetate.

4. The method of claim 1 wherein the aqueous suspension being preserved is a water-based paint.

5. The method of claim 1 wherein the aqueous suspension being preserved is a water-based paint, and the quaternary ammonium compound is formed by the reaction of hexamethylenetetramine and chloroacetic acid.

6. The method of claim 1 wherein the aqueous suspension being preserved is a water-based paint and the quaternary ammonium compound is formed by the reaction of hexamethylenetetramine and sodium chloroacetate.

7. The method of claim 1 wherein the aqueous emulsion or solution being preserved is a cutting fluid.

8. The method of claim 1 wherein the aqueous emulsion or solution being preserved is a cutting fluid, and the quaternary ammonium compound is formed by the reaction of hexamethylenetetramine and chloroacetic acid.

9. The method of claim 1 wherein the aqueous emulsion or solution being preserved is a cutting fluid, and the quaternary ammonium compound is formed by the reaction of hexamethylenetetramine and sodium chloroacetate.

10. The method of claim 1 wherein the aqueous suspension being preserved is a water-based paint and the quaternary ammonium compound is formed by the reaction of hexamethylenetetramine and chloroacetamide.

11. The method of claim 1 wherein the aqueous emulsion being preserved is a cutting fluid, and the quaternary ammonium compound is formed by the reaction of hexamethylenetetramine and chloroacetamide.

* * * * *

UNITED STATES PATENT AND TRADEMARK OFFICE
CERTIFICATE OF CORRECTION

PATENT NO. : 4,505,831
DATED : March 19, 1985
INVENTOR(S) : JOSEPH G. FENYES ET AL.

It is certified that error appears in the above-identified patent and that said Letters Patent is hereby corrected as shown below:

Column 1, the last two lines from the bottom, after "salts" insert --.--, and delete "whch can be represented by the formula".

Column 2, lines 1-10, delete the formula.
line 11, delete the line in its entirety.
line 12, delete "paragraph.".

Signed and Sealed this

Twenty-third Day of July 1985

[SEAL]

Attest:

DONALD J. QUIGG

*Attesting Officer*      *Acting Commissioner of Patents and Trademarks*